United States Patent [19]

Higashi et al.

[11] Patent Number: 4,906,670

[45] Date of Patent: Mar. 6, 1990

[54] PHARMACEUTICAL COMPOSITION FOR THE TREATMENT OF PERIODONTAL DISEASE

[75] Inventors: Kiyotsugu Higashi, Gojo; Shigeru Kametaka, Kashiwara; Reiko Izumi, Osaka; Katsuhiko Morisaki, Nara; Shin'ichi Hayashi, Fujiidera, all of Japan

[73] Assignee: Rohto Pharmaceutical Co., Ltd., Osaka, Japan

[21] Appl. No.: 317,077

[22] Filed: Mar. 1, 1989

Related U.S. Application Data

[63] Continuation of Ser. No. 29,550, Mar. 24, 1987, abandoned.

[30] Foreign Application Priority Data

Mar. 25, 1986 [JP] Japan .................................. 61-67813

[51] Int. Cl.$^4$ ................................................ A61K 9/06

[52] U.S. Cl. ..................................... 514/773; 514/781; 514/900; 514/902; 514/969

[58] Field of Search ............... 514/773, 781, 900, 902, 514/969

[56] References Cited

U.S. PATENT DOCUMENTS

| | | | |
|---|---|---|---|
| 3,839,590 | 10/1974 | Battista | 514/969 |
| 4,391,798 | 7/1983 | Tavss et al. | 424/49 |
| 4,517,173 | 5/1985 | Kizawa et al. | 424/435 |
| 4,725,428 | 2/1988 | Miyahara et al. | 424/49 |
| 4,725,671 | 2/1988 | Chu et al. | 514/801 |
| 4,764,377 | 8/1988 | Goodson | 424/435 |

*Primary Examiner*—Shep K. Rose
*Attorney, Agent, or Firm*—Robbins & Laramie

[57] ABSTRACT

A pharmaceutical composition useful for treatment of periodontal diseases which comprises one or more active ingredients effective for the treatment of periodontal diseases, characterized in that said active ingredient or ingredients are dispersed in collagen.

11 Claims, 1 Drawing Sheet

PHARMACEUTICAL COMPOSITION FOR THE TREATMENT OF PERIODONTAL DISEASE

This application is a continuation of application Ser. No. 029,550, filed Mar. 24, 1987, now abandoned.

This invention relates to a pharmaceutical composition useful for the treatment of periodontal diseases. More particularly, it relates to a pharmaceutical composition which comprises one or more active ingredients useful for the treatment of periodontal diseases, said active ingredient(s) being dispersed in collagen.

The "periodontal diseases" is a general term of various inflammatory diseases of paradentium. The diseases include a series of diseases exhibiting various syndromes which vary from each other according to the stage or situation of the diseases or the age of the patient, and have not been definitely subclassified. Since, however, the term "periodontal diseases" is given to any inflammatory disease which initially occurs at a marginal gingiva area and finally reaches an alveolar bone, the diseases can be roughly divided, on the basis of the degree of the inflammation, into "gingivitis" in which the inflammation is limited to the gingiva tissue, and "paradentitis" in which the inflammation is chronic and found even in an alveolar bone. However, peculiar diseases such as "juvenilie paradentitis" and "acute necrotizing ulcerative gingivitis" are also included in the periodontal diseases.

The paradentitis, which was once called "alveolar pyorrhea", is characterized by remarkable symptoms such as inflammation of gingiva, formation of periodontal pockets, bleeding and pus discharge from said periodontal pockets, and it brings about resorption of alveolar bone, loose tooth, and shedding of tooth.

The consensus of most investigators is that the periodontal diseases is caused by bacteria present in dental plaques formed in periodontal pockets. Efforts have been concentrated on the discovery of pathogenic bacteria responsible for said diseases. At the present time, an attributable major pathogen is recognized to be a certain nigral pigment-producing bacteria, such as genus Bacteroides. However, other genus of bacteria including Actinobacillus, Capnocytophaga, Fusobacterium and Spirochetes may be included in the causative pathogens. In any case, it is an established theory that the periodontal diseases should not be attributed to all bacteria present in the dental plaque.

It is considered that many factors are involved in the destruction of paradentium which is caused by pathogenic bacteria, and that the destruction is induced by two mechanisms. One is a direct action of various enzymes or cytotoxins produced by bacteria (e.g., endotoxins, peptidoglycans, acids, and the like), and the other is an indirect action due to an immune response of the host against the immunogenic substances just mentioned. Among them, the direct action of bacterial enzymes, especially collagenase, plays an important role in the destruction of the paradentium. Collagenase is a protease which mainly produced by microorganisms such as Bacteroides, and it cleaves collagen specifically. Accordingly, it is generally recognized that collagen fibers, the major component of the paradentium, are primarily destroyed by said enzyme. In fact, many literatures have been published in connection with the correlation between the collagenase and the periodontal diseases. For example, during pathological research of the diseases, it was observed that the disruption of the collagen fiber surrounding the vessel in tunica propria of gingival mucosa was increased with the progression of disease. On the other hand, it was shown that the collagenase activity in the periodontal effusion and gingival tissues was increased with the progression of the disease. In addition, Kowashi et al., Aroc. Oral. Biol., 24, 645, 1979, reported that during the investigation of experimental gingivitis induced by stopping tooth brushing, they observed that the collagenase activity in the effusion of gingival sulcus was increased with the progression of gingivitis, while the remission of disease and the reduction of collagenase activity were observed when the oral cavity was cleaned.

As will be understood from the above description, collagenase plays a very important role in the destruction of the paradentium.

It is known that collagenase is also produced by several activated cells responsible for an immune response, for example, macrophages, polymorphocytes and fibroblasts, which migrate to the locus of the paradentium for attacking bacteria or bacterial somatic components (e.g., lipopolysaccharides, peptidoglycans, and the like). Collagenase thus provided from different sources, i.e., bacteria and body cells, acts degradatively on the collagen fibers composing various tissues, such as gingiva, perivascular tissues, periodontal tissues, and alveolar bones, and brings the periodontal diseases to an advantage stage.

The periodontal diseases has previously been treated by several ways, such as exhaustive scaling of plaques in periodontal pockets, root plainning, gingivectomy to eliminate the periodontal pocket, or surgical curettage to excise inflammatory tissues. These treatments have been effective to some extent but not satisfactory.

On the other hand, pharmacotherapy has also been conducted using a drug selected from germicides, anti-inflammatory agents, plaque solubilizing agents, hemostyptics, and the like. These drugs are used in the form of the formulation suited for internal use or massotherapy (e.g., dentifrices, ointments, and the like). However, they are not satisfactory for the purpose of treatment of periodontal diseases because the internal use hardly permits the selective migration of the drug to the lesional region, and the massotherapy is not successful in solubilizing the plaques which are present beneath the gingival margin.

Recently, several strips which comprise polymers and active ingredients for treatment of periodontal diseases have been developed. These strips are said useful for the treatment of plaques and inflammation beneath the gingival margin. The strips can be applied directly to the lesional region to be treated, and therefore, the active ingredient can be concentrated to the desired site selectively. This modified therapeutic method has been proved to be more effective than any conventional pharmacotherapy. For instance, J. M. Goodson et al. disclose the implantation of "hollow fiber", which contains germicides, into gingival region (J. Clinical Periodontology, 1979: 6: 83–92). M. Addy et al. have reported the insertion of strips, which were prepared from a mixture of an insoluble polymer such as polyethylmethacrylate and germicides, into periodontal pockets (J. Periodontal, 693, Nov. 1982). In addition, insertion of the strips, prepared from a mixture of a soluble polymer and a drug, into the lesional region, such as periodontal pockets, is also reported (Japan Patent Publication No. 59-222406).

Attention has been paid to the fact that the periodontal diseases is characterized in that the progression of the diseases is always accompanied by the increase of collagenase activity in the lesional region.

On the basis of the above fact, a novel pharmaceutical composition has been prepared by dispersing in collagen an active ingredient effective for the treatment of periodontal diseases, and it has been found that the composition, which has been applied to the lesional region, is successfully disintegrated by collagenase present in the region and allowed to release the active ingredient, which in turn, prevents the collagen fiber of tissues from the proteolytic degradation. It has been also found that collagen itself exhibits a protective action against the disintegration of paradentium due to periodontal diseases.

This invention is based on the above findings and provides a pharmaceutical composition useful for the treatment of periodontal diseases which comprises one or more active ingredients effective for the treatment of said diseases, said active ingredient(s) being dispersed in collagen.

The composition of the invention is applied directly to periodontal region or pocket in the form of film, sheet, stick, gel or ointment.

Figure 1:
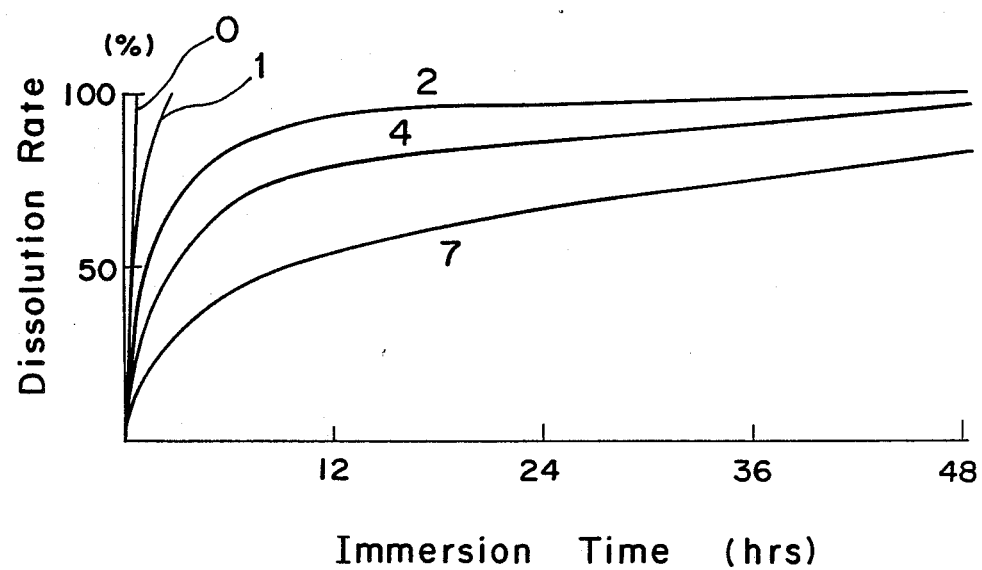
FIG. 1 shows the dissolution rate of the active ingredient from the compositions of the invention, which were subjected to crosslikage treatment.

Collagen employed in the invention may be a water soluble or insoluble collagen which is obtainable, by extraction, from various sources such as animal tissues. Collagen employed in the present invention may be one which has been chemically modified, provided that it retains the cleavage site of collagenase. Examples of such chemically modified collagen include atelocollagen, which is soluble in water and can be obtained by cleaving the telopeptide chain of collagen, and its derivatives prepared by succinylation or methylation. Atelocollagen is most preferred among others because of its several convenient characteristics described below:

(1) Exhibiting no antigenicity since the telopeptide chain responsible for immuno-activity has been removed;

(2) Having good affinity to vital tissues;

(3) Stimulating bio-synthesis or metabolism of collagen;

(4) Having an action to accelerate the healing of wounded connective tissues and formation of epithelial tissues;

(5) Capable of being easily modified by, for example, formation of cross linkage by the use of chemical agents such as glutaraldehyde, or irradiation of ultraviolet light or rays, whereby the release rate of active ingredients can be easily controlled.

As will be understood from the above descriptions, the composition of the invention may be prepared using any kind of collagen as far as they possess a cleavage site which is recognized and cleaved by collagenase. Accordingly, for the purpose of the invention, the term "collagen" herein used includes all kinds of collagens of different sources and derivatives thereof, which can be cleaved by collagenase.

As stated above, collagen is very useful as a carrier for pharmaceutical compositions, from the view point that it is decomposed by collagenase in oral cavity, whereby an active ingredient contained in the composition is allowed to release. However, it should be emphasized that collagen itself exhibits a protective action against the destruction of paradentium as illustrated in Experiment 3. Accordingly, the use of collagen as a carrier or base in the present invention provides a great convenience.

Therapeutically active ingredient or ingredients used for the preparation of the composition of the invention are selected from those effective for prevention or treatment of periodontal diseases, for example, germicides, such as chlorhexidine, Ag protein, glyceryl iodide, phenol, benzalkonium chloride, cetylpyridinium chloride, and the like; antimicrobial agents, such as ampicillin, tetracycline, benzylpenicillin, clindamycin, cefalexin, erythromycin, chloramphenicol, fragiomycin sulfate, and the like; anti-inflammatory agents, such as ibuprofen, indomethacin, ketoprofen, mefenamic acid, antipyrine, pranoprofen, ibufenac, tiaramide hydrochloride, prednisolone, dexamethasone, triamcinolone acetonide, prostaglandin, and the like; plaque solubilizing agents, such as dextranase, protease, amylase and the like; collagenase inhibitors obtained from the extraction of crude drugs, such as gambir-catechu known in the name of "asenyaku"; local anesthetics, such as tetracaine hydrochloride, ethyl aminobenzoate, and the like; antihistaminic agents, such as chlorphenyramine maleate, diphenhydramine, and the like; hemostatic agents such as tranexamic acid, and the like.

In preparing the pharmaceutical composition of the present invention, collagen is mixed with one or more of active ingredients and, if necessary, together with one or more of conventional excipients, and the mixture is formed into various preparations such as film, sheet, stick, gel or ointment in accordance with conventional methods. If desired, cross linkage formation may be done during preparation.

The composition of the invention in the form of film, sheet or bar can be prepared in different sizes. However, the convenient size of the film or sheet may be 0.1–0.5 mm in thickness, 0.5–3 mm in width, and 10–50 mm in length. The size of the bar may generally range from 0.5 to 1.5 mm in diameter and from 10 to 50 mm in length. Furthermore, the composition of the invention may be cut in suitable size by the user depending on several factors, such as severity of the disease, and the width and depth of the locus to be applied.

The composition may include pharmaceutically acceptable plasticizers, preservatives, pH regulating agents, base materials for preparing film or ointment, lubricants and/or stabilizers.

Following examples illustrate the preparation of the composition of the present invention. In examples, part or parts are represented by weight basis.

EXAMPLE 1

Tetracycline hydrochloride (2 parts) were dissolved or dispersed into an aqueous solution of succinylated atelocollagen (1 part) dissolved in water (100 parts), and the resultant mixture was subjected to deaeration to obtain a gel preparation.

EXAMPLE 2

The gel preparation obtained in Example 1 was air-dried to obtain a film. The film was treated with glutaraldehyde in a gaseous phase for 2 days to form a crosslinkage and then ground into powder. To the mixture of the powder (1 part) and hydroxypropyl cellulose (9 parts) was added a small amount of water and mixed throughly. The mixture was extruded, and the resultant product was dried to obtain a bar of 0.5 mm in diameter.

EXAMPLE 3

The powder (2 parts) obtained in Example 2 was mixed with plasti-base (4 parts) and sodium carboxymethyl cellulose (3 parts) to obtain an ointment.

The composition of the invention was examined for the controlled release of the active ingredient. In addition, the influence of collagen on paradentium and the relationship between controlled release of the active ingredient and the collagenase-activity in oral cavity were also studied as described below.

EXPERIMENT 1

Determination of Dissolution Rate of Active Ingredient from Film Preparation

1. Film Preparation

Atelocollagen was dissolved in a HCl solution (pH 3.5) to obtain a 2% aqueous solution of collagen. To the solution was added tetracycline hydrochloride (2% by weight relative to dried collagen), and the mixture was deaerated, casted on a Teflon tray, and dried to obtain a film of 100 micron in thickness. The film was cut into several fragments, which were neutralized with ammonia and then exposed to glutaraldehyde in gaseous phase for 0, 1, 2, 4 and 7 days.

2. Dissolution Test

The dissolution profiles of the active ingredient released from the fragments (1×1 cm) obtained above were measured using a phosphate buffer (500 ml), pH 7.2, at 37° C., in accordance with the Rotating Basket Method (100 rpm) of Japanese Pharmacopoeia (X). The control test was conducted using the fragment before crosslinking treatment.

3. Results

The results are shown in FIG. 1 of the accompanying drawing, which shows the time course of the dissolution rate of the active ingredient from the fragments which were subjected to crosslinkage treatment for different periods of time. The vertical and horizontal axes show dissolution rate and immersion time (hours), respectively. The numerals in the figure represent the period (days) of the glutaraldehyde treatment. FIG. 1 shows that the dissolution rate of the active ingredient from the fragment can efficiently be controlled and regulated by crosslinking treatment with glutaraldehyde.

EXPERIMENT 2

Correlation between Collagenase Activity and Dissolution Rate of Active Ingredient 1. Procedures The film fragments (1cm×1cm×100μ) exposed to glutaraldehyde for 4 days in accordance with Experiment 1 were each immersed at 37° C., for 2 hours, into a phosphate buffer (pH 7.2) and two phosphate buffers containing 0.1 μg/ml and 1.0 μg/ml of collagenase respectively, and dissolution rate of the active ingredient was determined for each sample.

2. Results

The results are shown in table 1.

TABLE 1

| Concentration of Collagenase (μg/ml) | 0 | 0.1 | 1.0 |
|---|---|---|---|
| Dissolution Rate | 46% | 51% | 58% |

The table shows that the release rate (dissolution rate) of the active ingredient from the film varies depending on the collagenase activity.

EXPERIMENT 3

Determination of Therapeutical Effects of Collagen on Periodontal Diseases in Hamster 1. Procedures Periodontal diseases was induced in hamsters by the use of *Actinomyces viscosus* ATCC 15987 (H. V. Jodan et al., Am. J. Path., 46, 843 (1965)). A 2% aqueous solution of atelocollagen (0.1 ml/kg weight) was applied to the periodontal regions of five hamsters every four days over one month. An aqueous CMC solution (1%, 0.1 ml/kg weight) was applied to 5 animals in the same manner as a control. Pathological changes around the periodontal regions of the animals which were treated with atelocollagen were investigated and compared with those of the control group.

2. Results

The hamsters treated with atelocollagen were significantly protected from the degradation of paradentium as compared with the control group.

What is claimed is:

1. In the art of applying active ingredients useful for the treatment of periodontal disease dispersed in collagen in order to protect against increased collagenase activity which always accompanies progression of periodontal disease, directly to the periodontal pocket, the improvement consisting of the step of placing in said periodontal pocket an extruded bar, film or ointment of periodontal agent dispersed in glutaraldehyde crosslinked succinylated atelocollagen gel in a 1 to 9 ratio with hydroxypropylcellulose.

2. The method of claim 1 wherein the active ingredient is selected from the group consisting of those active ingredients useful for the treatment of gingivitis, paradentitis, juvenile paradentitis and acute necrotizing ulcerative gingivitis.

3. The method of claim 1 wherein said active ingredient is selected from the group consisting of a germicide, an antimicrobial agent, an anit-inflammatory agent, a plaque solubilizing agent, a collagenase inhibitor, a local anesthetic, an antihistaminic agent and a hemostatic agent.

4. The method of claim 3 wherein the germicide is selected from the group consisting of chlorhexidine, silver protein, glycerol iodide, phenol, benzalkonium chloride and cetylpyridinium chloride.

5. The method of claim 3 wherein the antimicrobial agent is selected from the group consisting of ampicillin, tetracycline, benzylpenicillin, clindamycin, cefalexin, erthomycin, chloramphenicol and fragiomycin sulfate.

6. The method of claim 3 wherein the anti-inflammatory agent is selected from the group consisting of ibuprofen, indomethacin, ketoprofen, mefenamic acid, antipyrine, pranoprofen, ibufenac, tiaramide hydrochloride, prednisolone, dexamethasone, triamicinolone acetonide and prostaglandin.

7. The method of claim 3 wherein the plaque solubilizing agent is selected from the group consisting of dextranase, protease and amylase.

8. The method of claim 3 wherein the collagenase inhibitor is extracted from gambircatechu.

9. The method of claim 3 wherein the local anesthetic is selected from the group consisting of tetracaine hydrochloride and ethyl aminobenzoate.

10. The method of claim 3 wherein the antihistaminic agent is selected form the group consisting of chlorphenyramine maleate and dipenhydramine.

11. The method of claim 3 wherein the hemostatic agent is tranexamic acid.

* * * * *